United States Patent [19]

Sigg-Grütter et al.

[11] 4,088,688

[45] May 9, 1978

[54] PROCESS FOR MAKING HUMULONES AND NOVEL INTERMEDIATES THEREFOR

[75] Inventors: Trudi Sigg-Grütter, Winterthur; Jöst Wild, Porrentruy, both of Switzerland

[73] Assignee: Givaudan Corporation, Clifton, N.J.

[21] Appl. No.: 657,816

[22] Filed: Feb. 13, 1976

Related U.S. Application Data

[62] Division of Ser. No. 606,813, Aug. 22, 1975, Pat. No. 4,012,447.

[30] Foreign Application Priority Data

Sep. 9, 1974 Switzerland ............... 12156/74
Aug. 1, 1975 Switzerland ............... 10093/75

[51] Int. Cl.$^2$ .................. C07C 45/00; C07C 45/16
[52] U.S. Cl. .................. 260/586 D; 260/592
[58] Field of Search .................. 260/586 D

[56] References Cited

U.S. PATENT DOCUMENTS 3,552,975  1/1971  Worden et al. ............ 260/586 D
3,923,897  12/1975  Worden ................... 260/586 D

*Primary Examiner*—Norman Morgenstern
*Attorney, Agent, or Firm*—Thomas Cifelli, Jr.; Robert F. Tavares

[57] ABSTRACT

Humulones (I) are made by subjecting desoxyhumulones (II) to oxidation to form novel hydroperoxides (III) and reducing the latter.

The humulones are used to make known isohumulones (IV) which are bitter substances useful in the beverage industry.

10 Claims, No Drawings

PROCESS FOR MAKING HUMULONES AND NOVEL INTERMEDIATES THEREFOR

This is a division of application Ser. No. 606,813, filed Aug. 22, 1975, now U.S. Pat. No. 4,012,447.

FIELD OF THE INVENTION

This invention relates to the beverage field, e.g., the beer industry.

SUMMARY OF THE INVENTION

The humulones manufactured according to the present invention are compounds of the general formula

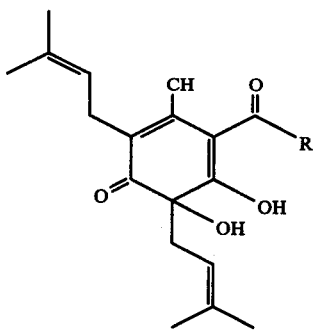

(I)

where R represents a $C_{1-6}$ alkyl group.

According to the present invention, the compounds of formula I hereinbefore are manufactured by oxidising a compound of the general formula

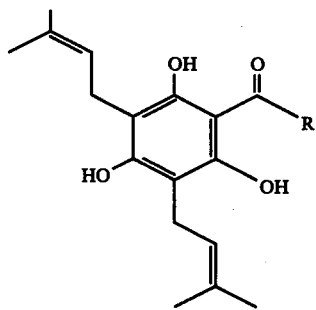

(II)

wherein R has the significance given earlier, to give a hydroperoxide of the general formula

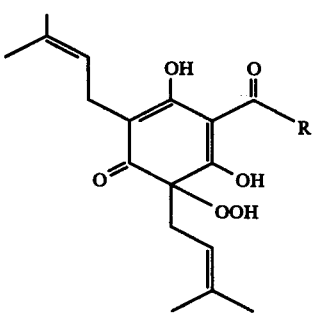

(III)

, wherein R has the significance given earlier, and subsequently reducing a hydroperoxide of formula III to give a compound of formula I.

The compounds of formula I are intermediates for the manufacture of known bitter substances of the general formula

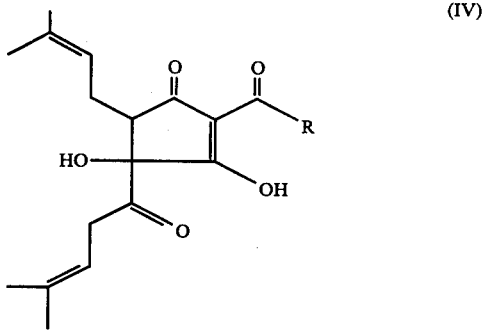

(IV)

, wherein R has the significance given earlier, into which they can be converted by isomerisation in a known manner.

The compounds of formula IV are of significance in the beverage industry; for example, in the brewing of beer. Thus, for example, in the brewing of beer, the humulone present in the hops (compound I with R = isobutyl) is converted into isohumulone (compound IV with R = isobutyl) during the boiling of the wort with the hops, by which means the pleasantly bitter flavour is imparted to the beer.

The process in accordance with the present invention enables the compounds of formula I and, thus, also the compounds of formula IV, to be manufactured in good yields, which hitherto has not been possible (Riedl. Chem. Berichte 85, 692–710, 1952).

DESCRIPTION OF THE PREFERRED EMBODIMENTS

Apart from the aforementioned isobutyl group, examples of $C_{1-6}$ alkyl groups are: methyl, isopropyl (compound I = cohumulone), sec-butyl (compound I = adhumulone), ethyl (compound I = posthumulone), isoamyl (compound I = prehumulone).

The hydroperoxides of formula III are novel and also form part of the present invention.

The oxidation of a compound of formula II to give a hydroperoxide of formula III is expediently carried out by means of elementary oxygen.

The process in accordance with the present invention (i.e. the conversion of a compound of formula II into a compound of formula I) is expediently carried out in the presence of a base and a polar aprotic solvent, preferably at a low temperature and especially at a temperature below 0° C (e.g. between 0° C and −50° C.

As bases there are preferably used very strong bases such as alkali metal alcoholates derived from lower tertiary alkanols (e.g. potassium t-butylate). However, alkali metal hydroxides (e.g. sodium hydroxide or potassium hydroxide) can also be used. The base is preferably used in excess; for example, in at least a 2-fold excess.

The nature of the polar aprotic solvent is not critical and, in practice, the choice is only limited by the fact that the solidification point thereof must lie below the relatively low temperature at which the process is carried out. Examples of suitable polar aprotic solvents are ethers (e.g. tetrahydrofuran), di(lower alkoxy)-(lower alkanes) (e.g. dimethoxyethane), amines such as di(- lower alkyl)amines (e.g. dimethylamine, nitriles (e.g. acetonitrile, amides such as N,N-di(lower alkyl)amides derived from lower aliphatic carboxylic acids (e.g. N,N-dimethylformamide and N,N-dimethylacetamide) phosphoric acid derivatives (e.g. hexamethylphosphoric acid triamide) etc.

Better yields are obtained by carrying out the process in an anhydrous medium, but the presence of a slight amount (i.e. a small percentage) of water does not substantially impair the yields.

For the reduction of a hydroperoxide of formula III to give a compound of formula I there are advantageously used reducing agents which satisfy the following requirements:

1. They should not be oxidised by oxygen under the conditions employed; and
2. They should, under the conditions employed, reduce the hydroperoxide of formula III so rapidly that it does not react with a compound of formula II or I and thus lead to losses in the yields.

Especially suitable reducing agents are tri(lower alkyl)phosphates such as, for example, triethylphosphite, trimethylphosphite or tributylphosphite.

According to a preferred embodiment of the process in accordance with the present invention, the oxidation of a compound of formula II and the reduction of a hydroperoxide of formula III are carried out in one and the same operation without isolation of the hydroperoxide of formula III; that is to say, the reducing agent is added to the mixture in toto or in part at the beginning of the process. For example, the reducing agent can be added to the mixture as the compound of formula II is consumed and the hydroperoxide of formula III is formed therefrom. The consumption of the compound of formula II can be followed, for example, by chromatography (e.g. thin-layer chromatography).

According to a further preferred embodiment of the present process, an alcohol (e.g. a lower alkanol) is added to the mixture. Preferred alcohols are secondary and, in particular, tertiary alcohols. Examples are 2-propanol, 2-methyl-2-butanol and t-butanol.

The time required to complete the process can vary from several minutes to several hours (e.g. 10 hours).

The course of the process can be followed analytically (e.g. by thin-layer chromatography).

The isolation of the compounds of formula I from the mixture can be carried out according to methods known per se; for example, by extraction of the mixture diluted with a mineral acid (e.g. dilute hydrochloric acid or dilute sulphuric acid) using an organic solvent such as an ether.

Where a compound of formula I is to be subsequently isomerised to a compound of formula IV, isolation is not necessary since the mixture can be directly subjected to this isomerisation.

The following Examples illustrate the present invention:

EXAMPLE 1

6.64 g of desoxy-cohumulone (compound II with R = isopropyl), 5.6 g of potassium t-butylate, 3.65 g of triethylphosphite, 30 ml of N,N-dimethylformamide and 20 ml of t-butanol are added under a nitrogen atmosphere to a sulphonation flask which is provided with a stirrer, gas delivery tube and thermometer. The mixture is cooled to $-30°$ C and oxygen is led in instead of nitrogen. After stirring for 3 hours, desoxy-cohumulone is no longer present according to thin-layer chromatographic analysis. Nitrogen is now again led in in place of oxygen and there are carefully added to the mixture 100 ml of 2-N hydrochloric acid. The mixture is extracted three times with 500 ml of dimethyl ether. The combined diethyl ether extracts are washed four times with 250 ml of ice-water each time, dried over sodium sulphate and concentrated under reduced pressure at 30° C. There are obtained 8.92 g of crude product which, according to chromatographic analysis, contains 6.4 g of cohumulone. The by-products consist almost exclusively of triethylphosphate which can be separated by distillation at 75° C/0.01 mm Hg.

The most important data from 24 further Examples are given in the following Table. Example 1 hereinbefore has been included in this Table as No. 1. The amount of starting material of formula II is 10 mmol in all Examples with the exception of Example 1 in which the amount is 20 mmol.

Examples 1–25

| No. | Compd. II R | Oxidising agent | Base | Solvent | Reducing agent | Alcohol | Temp. °C | Time hours | Crude product | Compd. I g | Remarks |
|---|---|---|---|---|---|---|---|---|---|---|---|
| 1 | i-$C_3H_7$ | $O_2$ | K t-butylate | Dimethyl-formamide | Triethyl-phosphite | t-Butanol | −30 | 3 | 8.92 | 6.4 | |
| 2 | i-$C_3H_7$ | $O_2$ | K -butylate | Dimethyl-formamide | Triethyl-phosphite | t-Butanol | 0 | 1.25 | 4.22 | 2.31 | |
| 3 | i-$C_3H_7$ | $O_2$ | K t-butylate | Dimethoxy-ethane | Triethyl-phosphite | t-Butanol | −30 | 3 | 3.9 | 2.65 | |
| 4 | i-$C_3H_7$ | $O_2$ | K t-butylate | Tetrahydro-furan | Triethyl-phosphite | t-Butanol | −25 | 6.5 | 5.55 | 2.66 | Acidification with $H_2SO_4$ |
| 5 | i-$C_3H_7$ | $O_2$ | KOH | Dimethyl-formamide | Triethyl-phosphite | t-Butanol | −30 | 5 | 4.68 | 2.89 | |
| 6 | i-$C_3H_7$ | $O_2$ | K t-butylate | Hexamethyl-phosphoric acid tri-amide | Triethyl-phosphite | t-Butanol | −25 −30 | 2.63 | 4.72 | 2.89 | |
| 7 | i-$C_3H_7$ | $O_2$ | K t-butylate | Aceto-nitrile | Triethyl-phosphite | t-Butanol | −25 −30 | 3 | 4.75 | 1.6 | |
| 8 | i-$C_3H_7$ | Air | K t-butylate | Dimethyl-formamide | Triethyl-phosphite | t-Butanol | −25 −35 | 5 | 4.66 | 2.76 | |
| 9 | i-$C_3H_7$ | $O_2$ | K t-butylate | Dimethyl-formamide | Triethyl-phosphite | Ethanol | −30 | 7 | 4.17 | 1.01 | |
| 10 | i-$C_3H_7$ | $O_2$ | K t-butylate | Dimethyl-formamide | Triethyl-phosphite | 2-Propanol | −25 −30 | 6.75 | 4.53 | 2.39 | |
| 11 | i-$C_3H_7$ | $O_2$ | K t-butylate | Dimethyl-formamide | Tri-methyl phosphite | t-Butanol | −28 | 3 | 3.7 | 2.54 | |
| 12 | i-$C_3H_7$ | $O_2$ | K t-butylate | Dimethyl-amine | Triethyl-phosphite | t-Butanol | −50 | 5.5 | 4.24 | 2.19 | |
| 13 | i-$C_3H_7$ | $O_2$ | K t-butylate | Dimethyl-formamide | Triethyl-phosphite | — | −30 | 1.5 | 4.39 | 2.17 | |

Examples 1-25-continued

| No. | Compd. II R | Oxidising agent | Base | Solvent | Reducing agent | Alcohol | Temp. °C | Time hours | Crude product | Compd. I g | Remarks |
|---|---|---|---|---|---|---|---|---|---|---|---|
| 14 | i-C$_3$H$_7$ | O$_2$ | K t-butylate | Dimethyl-formamide | Triethyl-phosphite | 2-Methyl-2-butanol | −25 −30 | 6 | 4.53 | 2.72 | |
| 15 | i-C$_3$H$_7$ | O$_2$ | K t-butylate | Dimethyl-formamide | Triethyl-phosphite | t-Butanol | −15 | 1.25 | 4.77 | 2.6 | |
| 16 | i-C$_3$H$_7$ | O$_2$ | K t-butylate | Dimethyl-formamide | Triethyl-phosphite | t-Butanol | −25 −30 | 2 | 4.59 | 2.7 | +1 ml H$_2$O |
| 17 | i-C$_3$H$_7$ | O$_2$ | K t-butylate | Dimethyl-formamide | Triethyl-phosphite | t-Butanol | −20 | 1 | 4.9 | 2.6 | |
| 18 | i-C$_3$H$_7$ | O$_2$ | K t-butylate | Dimethyl-sulfoxide | Triethyl-phosphite | t-Butanol | −5 0 | 0.5 | 4.25 | 2 | |
| 19 | i-C$_3$H$_7$ | O$_2$ | K t-butylate | Dimethyl-formamide | Triethyl-phosphite | t-Butanol | −40 −50 | 5.5 | | 3.27 | |
| 20 | i-C$_3$H$_7$ | O$_2$ | KOH | Dimethyl-formamide | Triethyl-phosphite | — | −25 −30 | 1 | 4.75 | 3.41 | |
| 21 | i-C$_3$H$_7$ | O$_2$ | KOH | Dimethyl-formamide | Triethyl-phosphite | — | −10 | 0.5 | 4.7 | 3.27 | |
| 22 | i-C$_3$H$_7$ | O$_2$ | KOH | Dimethyl-formamide | Triethyl-phosphite | — | −5 | 0.5 | 4.15 | 2.75 | |
| 23 | i-C$_3$H$_7$ | O$_2$ | K t-butylate | Dimethyl-acetamide | Triethyl-phosphite | t-Butanol | −30 | 2.5 | 4.36 | 3.29 | |
| 24 | i-C$_4$H$_9$ | O$_2$ | K t-butylate | Dimethyl-formamide | Triethyl-phosphite | t-Butanol | −30 | 3 | 4.1 | 3.4 | |
| 25 | CH$_3$ | O$_2$ | K t-butylate | Dimethyl-formamide | Triethyl-phosphite | t-Butanol | −30 | 3 | 4 | 2.4 | |

EXAMPLE 26

Preparation and characterisation of the hydroperoxide of formula III (R = i-C$_3$H$_7$):

3 g of desoxy-cohumulone are dissolved in 700 ml of hexane, treated with 1 g of 10% palladium on active carbon (activated by hydrogen treatment) and oxidised at −20° C for 8 hours with air-oxygen. The mixture is filtered, the filtrate concentrated to ca 50 ml under a high vacuum (0.03 mm Hg) and at a maximum temperature of −20° C. This solution is chromatographed at −18° C. This solution is chromatographed at −18° C on silica gel [pre-washed with methanol/concentrated hydrochloric acid (9:1)] with pentane/ether (1:1). There is first eluted desoxy-cohumulone, then cohumulone and finally the hydroperoxide of formula III. From the thin-layer chromatogram [silica gel on glass, washed with methanol/concentrated hydrochloric acid (9:1); eluant: hexane/ether (1:1)] 1% (V/V) glacial acetic acid), the individual fractions produce the following results:

| | Rf - value | FeCl$_3$ reaction |
|---|---|---|
| Desoxy-cohumulone | 0.55 | black |
| Cohumulone | 0.42 | blue |
| Hydroperoxide of formula III | 0.24 | violet |

The fractions containing the hydroperoxide of formula III are combined, evaporated in vacuo at −20° C and the residue is taken up in deutero-acetone. From the NMR spectrum of this solution [60 MHz; −20° C; TMS (tetramethylsilane) as the internal standard], the following data can be produced on the chemical shifts in comparison to cohumulone:

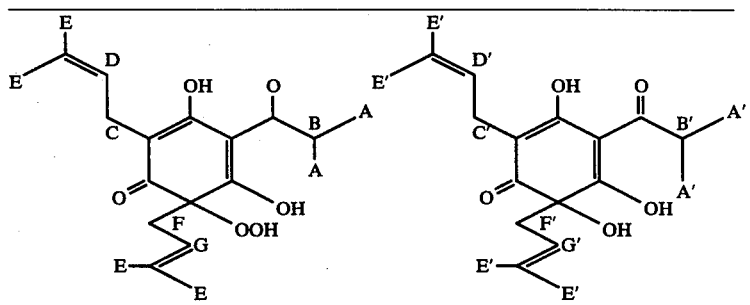

A 0.95 - 1.37 ppm, m
B 3.92 ppm, m, I = 6.5 Hz
C 3.15 ppm, d, I = 7 Hz
D 5.18 ppm, t, I = 7 Hz
E 1.45 - 1.85 ppm, m
F 2.52 ppm, d, I = 8 Hz
G 4.87 ppm, t, I = 8 Hz A' 0.95 - 1.30 ppm; m
B' 3.77 ppm, m
C' 3.09 ppm, d, I = 7 Hz
D' 5.17 ppm, t, I = 7 Hz
E' 1.45 - 1.85 ppm, m
F' 2.57 ppm, d, I = 8 Hz
G' 5.04 ppm, t, I = 8 Hz Mass spectrum:
Hydroperoxide III
m/e: 364 (3%); 296 (49%); 253 (31%); 181 (28%); 71 (40%); 69 (99%); 67 (18%); 59 (15%); 55 (16%); 53 (19%); 43 (89%); 41 (100%).
Cohumulone:
m/e: 348 (2%); 280 (11%); 224 (10%); 181 (9%); 69 (100%); 53 (14%); 41 (51%).

EXAMPLE 27

The solution of the hydroperoxide of formula III prepared according to Example 26 is evaporated at −20° C under a high vacuum. The residue is taken up in 10 ml of benzene. 1 ml portions of this solution are shaken respectively with the following reagents:
 a. dimethylsulphide, 0.5 ml;
 b. trimethylphosphite, 0.5 ml;
 c. 0.2 g of sodium iodide + 0.5 ml of acetic acid + 3 ml of water.

By thin-layer chromatography of the benzene solutions, it can be shown that in each case the hydroperoxide of formula III is reduced practically quantitatively to cohumulone. In the case of (c), the formation of elementary iodine can also be determined.

EXAMPLE 28

The procedure described in Example 26 is repeated using desoxyhumulone (compound II with R = isobutyl) as the starting material. The resulting hydroperoxide of formula III (R = isobutyl) shows a violet FeCl$_3$ reaction and gives the following mass spectroscopic data:

m/e: 378 (M$^{30}$), 310, 253, 85, 69, 57.

By reduction of this hydroperoxide (R = isobutyl) with dimethylsulphide in benzene there is obtained humulone of formula I (R = isobutyl).

EXAMPLE 29

The procedure described in Example 26 is repeated using desoxymethyl-humulone (compound II with R = methyl). The hydroperoxide of formula III (R = methyl) is purified by preparative column chromatography as described earlier and subjected to mass spectroscopic examination, the following values being obtained:

m/e: 336 (M$^+$), 268, 253, 69, 43.

What is claimed is:

1. A process for the manufacture of compounds of the formula:

(I)

wherein R represents a $C_{1-6}$ alkyl group, which process comprises oxidizing a compound of the general formula:

(II)

by means of elementary oxygen in the presence of a base and a a polar aprotic solvent at a temperature within the range from 0° C. to −50° C., to give a hydroperoxide of the formula (III)

and subsequently reducing a hydroperoxide of formula III to give a compound of formula I, by means of a tri (lower) alkyl phosphate in the presence of a base and a polar aprotic solvent at a temperature within the range from 0° C. to −50° C.

2. A process according to claim 1, wherein an alkali metal hydroxide or an alkali metal tertiary lower alkanolate is used as the base.

3. A process according to claim 1, wherein a trialkylphosphite is used as the reducing agent.

4. A process according to claim 1, wherein the oxidation of a compound of formula II to give a hydroperoxide of formula III is carried out in the presence of the reducing agent.

5. A process according to claim 1, wherein the oxidation is carried out in the presence of elementary oxygen, a trialkylphosphite is the reducing agent, and the oxidation and reduction are carried out at a temperature between 0° C. and −50° C.

6. A process according to claim 1, wherein the reaction is carried out in the presence of a base selected from the group consisting of alkali metal hydroxides and an alkali metal tertiary lower alkanolate and a polar aprotic solvent selected from the group consisting of ethers, di(lower alkoxy)-(lower alkanes), di(lower alkyl)amines, nitriles, amides and phosphoric acid derivatives.

7. A process according to claim 1, wherein a compound of formula II in which R represents the methyl group is used as the starting material.

8. A process according to claim 5, wherein a compound of formula II in which R represents the isopropyl group is used as the starting material.

9. A process according to claim 5, wherein a compound of formula II in which R represents the isobutyl group is used as the starting material.

10. A process according to claim 5, wherein a compound of formula I in which R represents the sec.-butyl group is used as the starting material.

* * * * *